United States Patent [19]

McQuaid et al.

[11] Patent Number: 5,153,196

[45] Date of Patent: Oct. 6, 1992

[54] EXCITATORY AMINO ACID RECEPTOR ANTAGONISTS AND METHODS FOR THE USE THEREOF

[75] Inventors: Loretta A. McQuaid; Charles H. Mitch; Paul L. Ornstein; Darryle D. Schoepp; Edward C. R. Smith, all of Indianapolis, Ind.

[73] Assignee: Eli Lilly and Company, Indianapolis, Ind.

[21] Appl. No.: 710,649

[22] Filed: Jun. 5, 1991

[51] Int. Cl.$^5$ .................. A61K 31/30; A61K 31/495
[52] U.S. Cl. ................................................ 514/250
[58] Field of Search ........................................ 514/250

[56] References Cited

U.S. PATENT DOCUMENTS

| | | | |
|---|---|---|---|
| 3,764,681 | 10/1973 | Dreikorn | 424/258 |
| 3,953,457 | 4/1976 | Dreikorn et al. | 260/288 |
| 3,979,387 | 9/1976 | Dreikorn et al. | 260/250 |
| 3,987,196 | 10/1976 | Dreikorn | 424/250 |
| 4,008,322 | 2/1977 | Dreikorn et al. | 424/250 |
| 4,354,027 | 10/1982 | Loev et al. | 544/346 |
| 4,495,187 | 1/1985 | Sarges | 514/250 |
| 4,623,725 | 11/1986 | Kadin et al. | 544/346 |
| 4,902,687 | 2/1990 | Ornstein | 544/253 |
| 4,902,695 | 2/1990 | Ornstein | 514/307 |
| 4,968,678 | 11/1990 | Ornstein | 514/222.2 |

FOREIGN PATENT DOCUMENTS 0315959 5/1989 European Pat. Off. .
0348872 1/1990 European Pat. Off. .

OTHER PUBLICATIONS

DeStevens et al., *J. Org. Chem.*, 28, 1336-1339 (1963).
Field et al., *J. Org. Chem.*, 36, 2968-2972 (1971).
Makino et al., *Heterocycles*, 23, 2025-2034 (1985).
Loev et al., *J. Med. Chem.*, 28, 363-366 (1985).
Trivedi et al., *J. Med. Chem.*, 31, 1011-1014 (1988).
Francis et al., *J. Med. Chem.*, 31, 1014-1020 (1988).
Williams, "Adenosine Antagonists", *Medicinal Research Reviews*, vol. 9, No. 2, 219-243 (1989).
Ornstein and Schoepp, "Excitatory Amino Acid Receptor Antagonists as Potential Therapeutic Agents", *Current CNS Patents*, vol. 1, No. 6, p. 1 et seq.

Primary Examiner—S. J. Friedman
Attorney, Agent, or Firm—James P. Leeds; Leroy Whitaker; John C. Demeter

[57] ABSTRACT

Excitatory amino acid receptor antagonists and methods for the use thereof are disclosed. The antagonists include compounds having the preferred formula:

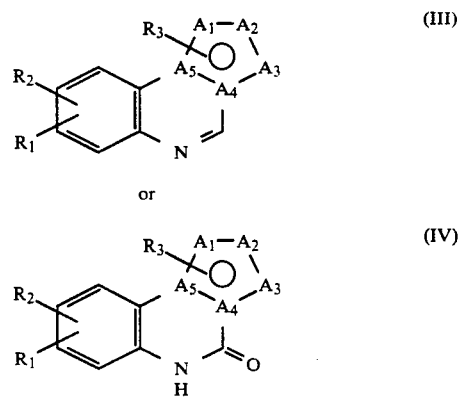

in which: each of $A_1$, $A_2$ and $A_3$ is independently either C or N, except that at least one of $A_1$, $A_2$ and $A_3$ is N; one of $A_4$ and $A_5$ is C and the other is N; each $R_1$ and $R_2$ is independently hydrogen, halogen, CN, $NO_2$, alkyl, aromatic, azido or $CF_3$; and $R_3$ is hydrogen, alkyl, aromatic or $CF_3$. Also included are the tautomers thereof, and the pharmaceutically acceptable salts of (III) and (IV) and the tautomers thereof. These compounds are useful as EAA antagonists for blocking one or more EAA receptors, as neurological disorders associated with EAA receptors.

18 Claims, No Drawings

EXCITATORY AMINO ACID RECEPTOR ANTAGONISTS AND METHODS FOR THE USE THEREOF

BACKGROUND OF THE INVENTION

1. Field of the Invention:

The present invention relates to the field of excitatory amino acid (EAA) receptor antagonists, and particularly to novel methods and compounds for blocking one or more EAA receptors.

2. Description of the Prior Art:

Excitatory amino acid receptors form a basic link for neurotransmission EAA receptors are of two general types, "ionotropic" and "metabotropic". Ionotropic receptors are directly coupled to the opening of cation channels in the cell membrane. There are at least three subtypes of ionotropic EAA receptors, namely those which are selectively activated by the agonists N-methy-D-aspartic acid (NMDA), 2-amino-3-(3-hydroxy-5-methylisoxazol-4-yl)propanoic acid (AMPA) and kainic acid (KA). Compounds that act as antagonists at the NMDA receptor complex can include compounds that act at the glutamate recognition site, the glycine recognition site, and the ion-channel binding site A G-protein or second messenger-linked "metahotropic" EAA receptor leads to enhanced phosphoinositide hydrolysis in the postsynaptic cell when activated by the agonists quisqualate, ibotenate or trans-1-aminocyclopentane-1,3-dicarboxylic acid.

Endogenous EAA receptor agonists include a number of substances that are found in the brain and spinal cord. The substances are all acidic amino acids, and include L-glutamic acid, L-aspartic acid, L-cysteic acid, L-homocysteic acid, L-cysteinesulfinic acid, L-homocysteinesulfinic acid, and quinolinic acid. Of these compounds, there is overwhelming evidence that L-glutamic acid and L aspartic acid mediate excitatory synaptic transmission at a substantial portion of all synapses throughout the central nervous system (CNS).

A number of selective, potent and bioavailable antagonists for excitatory amino acid receptors in the CNS have been discovered. A large body of data now shows that these agents are neuroprotective in animal models and may have therapeutic potential in the treatment of neurological disorders such as epilepsy, stroke, brain and spinal cord trauma, cerebral ischaemia, muscular spasms, neurodegenerative diseases and conditions including Huntington's chorea and dementia of the Alzheimer's type, Parkinson's disease, and Amyotrophic lateral sclerosis, anxiety, urinary incontinence, analgesia, muscle spasms, opiate tolerance and withdrawal, and as an antipsychotic. There remains a substantial need for the identification of new EAA receptor antagonists.

A variety of excitatory amino acid receptor antagonists have been identified in recent patents. In U.S. Pat. No. 4,902,687, issued Feb. 20, 1990 to Ornstein, there are described certain piperazine compounds useful as EAA receptor antagonists. The use of decahydroisoquinolines and piperidines, both of which may have tetrazole substitution, is described in U.S. Pat. Nos. 4,902,695 and 4,968,678, issued to Ornstein on Feb. 20, 1990 and Nov. 6, 1990, respectively. The use of heterocyclic dihydroxyquinoxaline and quinoxalinedione compounds as glutamate receptor antagonists for treating epilepsy, psychosis and dementia is described in European Patent Applications A1 348 872 and A2 315 959, respectively.

In U.S. Pat. No. 4,713,383, issued to Francis et al. on Dec. 15, 1987, there are disclosed certain [1,2,4]triazolo[1,5-c]quinazoline compounds which include a double-bonded moiety at the C5 position. Compounds with an oxygen or sulfur at this position are indicated to be useful as benzodiazepine antagonists; those with an imino group are indicated to be adenosine antagonists. Activity of the triazoloquinazolin-5-amines and -5-imines as adenosine antagonists is discussed in "Structure-Activity Profile of a Series of Novel Triazoloquinazoline Adenosine Antagonists", by Francis et al., in J. Med. Chem., v. 31, pp. 1014–1020 (1988). Similarly, the activity of certain triazoloquinoxalin-4-amines is presented in "[1,2,4]Triazolo[4,3-a]quinoxalin-4-amines: A New Class of $A_1$ Receptor Selective Adenosine Antagonists", by Trivedi et al., in J. Med. Chem., v. 31, pp. 1011–1014 (1988). See also, "Adenosine Antagonists", by Michael Williams, in Medicinal Research Reviews, v. 9, no. 2, pp 219–243 (1989).

Triazoloquinoxalin-4-ones are described in U.S. Pat. No. 4,354,027, issued to Loev et al. on Oct. 12, 1982, as being useful as anti-hypertensive agents. Use of the triazoloquinoxaline-diones is described in "1,2,4-Triazolo[4,3-a]quinoxaline-1,4-diones as Antiallergic Agents", by Loev, et al., in J. Med. Chem., v. 28, pp. 363–366 (1985). The use of [1,2,4]Triazolo[4,3-a]quinoxalin-4(5H)-ones as antidepressants and antifatique agents is described in European Patent Application EP 107455 A1, filed May 2, 1984.

SUMMARY OF THE INVENTION

Briefly describing one aspect of the present invention, there is provided a method for blocking one or more excitatory amino acid receptors which comprises administering a pharmaceutically effective amount of a compound having the general structure:

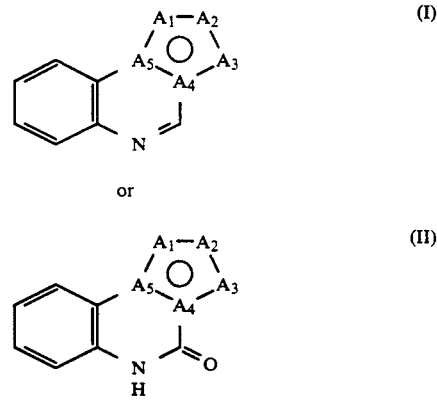

in which: each of $A_1$, $A_2$ and $A_3$ is independently either C or N except that at least one of $A_1$, $A_2$ and $A_3$ is N; and one of $A_4$ and $A_5$ is C and the other is N. In addition to this basic structure, the compounds preferably include at least one electron withdrawing group attached to the six-member carbon ring.

In a preferred embodiment the methods of the present invention comprise administering compounds having the general formula:

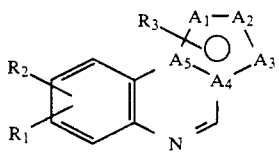

or

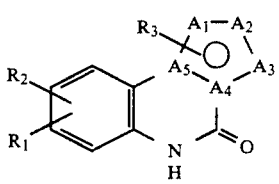

in which:

each of $A_{1-5}$ is as previously defined;

each of $R_1$ and $R_2$ is independently hydrogen, halogen, CN, NO$_2$, C$_1$-C$_4$ akyl, phenyl or fused benzo, azido, CF$_3$, NHSO$_2$R' with R' comprising C$_1$-C$_4$ alkyl or phenyl, or SO$_2$NR"R'" with each of R" and R'" being either H or a C$_1$-C$_4$ alkyl; and $R_3$ is hydrogen, alkyl, aromatic or CF$_3$.

For the foregoing $R_{1-3}$ and R' groups, any phenyl or fused benzo may optionally be substituted with hydrogen, halogen, CN, NO$_2$, C$_1$-C$_4$ alkyl, azido or CF$_3$. As used herein, the term "C$_1$-C$_4$ alkyl" represents a straight or branched alkyl chain having from one to four carbon atoms. Typical C$_1$-C$_4$ alkyl groups include methyl, ethyl, n-propyl, isopropyl, n-butyl, isobutyl, sec-butyl and t-butyl. Also, the term "halogen" includes chlorine, bromine, fluorine and iodine.

Also included are the tautomers thereof, and the pharmaceutically acceptable salts of (I)-(IV) and the tautomers thereof.

The present invention further includes methods for neuroprotection in mammals, and for the treatment of a variety of disorders linked to the EAA receptors including neurological disorders such as epilepsy, stroke, brain and spinal cord trauma, cerebral ischaemia, muscular spasms, neurodegenerative diseases and conditions including Huntington's chorea and dementia of the Alzheimer's type, Parkinson's disease, and Amyotrophic lateral sclerosis, anxiety, urinary incontinence, analgesia, muscle spasms, opiate tolerance and withdrawal, and as an antipsychotic.

The present invention further provides compounds, as well as pharmaceutical preparations, useful as EAA receptor antagonists and neuroprotective agents. Methods for the preparation of the foregoing compounds and pharmaceutical preparations are also provided.

It is an object of the present invention to provide novel compounds useful as antagonists for excitatory amino acid receptors. Another object of the present invention is to provide pharmaceutical formulations comprising the EAA receptor antagonists and a pharmaceutically acceptable carrier, diluent or excipient therefor.

It is a further object of the invention to provide methods of blocking one or more excitatory amino acid receptors, as well as methods for treating a variety of disorders which have been linked to the EAA receptors.

Further objects and advantages of the present invention will be apparent from the description which follows.

DESCRIPTION OF THE PREFERRED EMBODIMENT

For the purposes of promoting an understanding of the principles of the invention, reference will now be made to the embodiments described herein, and specific language will be used to describe same. It will nevertheless be understood that no limitation of the scope of the invention is thereby intended, such alterations, modifications and further applications of the principles of the invention as described herein being contemplated as would normally occur to one skilled in the art to which the invention relates.

EAA receptor antagonists are important compounds for use in research and in the treatment of CNS disorders. Prior to the present invention, a few antagonists had been identified, but there has remained a substantial need for the provision of new, and particularly selective, EAA receptor antagonists. In accordance with the present invention, there has been found a family of compounds which have been shown to be effective as EAA receptor antagonists. As such, these compounds are useful for treating CNS disorders, as neuroprotective agents and in research directed to further understanding of the central nervous system.

The compounds of the present invention are selected from the quinoxaline and quinazoline compounds having the basic structure (I), or the related carbonyl compounds (II):

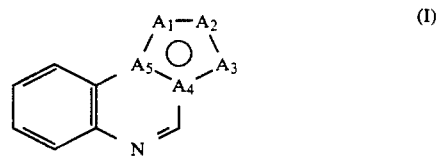

or

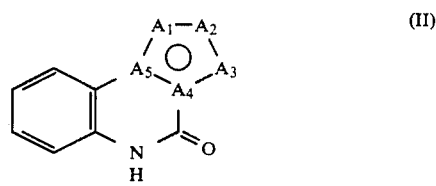

For such compounds, each of $A_{1-3}$ is independently either C or N, except that at least one of $A_{1-3}$ is N. One of $A_4$ and $A_5$ is C and the other is N. Substitution at various sites on these compounds is not required but is acceptable, provided that any substituents are non-interfering to the function of the compound for its uses described herein. It will further be understood that double bonds may appear within the five-member ring, depending on the location of the carbon and nitrogen atoms and any substituents thereon. Thus, the foregoing formulas describe the basic structures of the compounds useful in accordance with the inventive methods.

In a preferred aspect, the compounds used in the methods of the present invention may include substituents on the six member carbon ring and/or the five-member ring. A preferred substituent on the six member carbon ring is an electron withdrawing group. The compounds preferably have the structure:

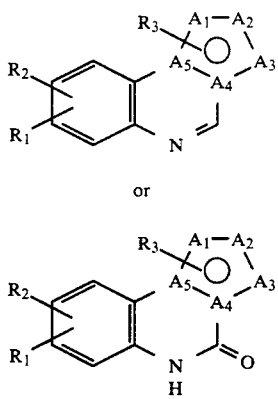

in which: each of $A_{1-5}$ is as previously defined; each of $R_1$ and $R_2$ is independently hydrogen, halogen, CN, $NO_2$, alkyl, aromatic, azido or $CF_3$; and $R_3$ is hydrogen, alkyl, aromatic or $CF_3$. As used herein, the term "aromatic" is used in its conventional manner to include unsaturated cyclic hydrocarbons, for example phenyl. Such groups may be attached by a single bond with one of the available carbons, or may be in the form of a fused ring sharing two adjacent carbons of the basic compound structure. In such case, $A_1$ and $A_2$ or $A_2$ and $A_3$ would both have to be carbon. Also included are the tautomers thereof, and the pharmaceutically acceptable salts of (I)–(IV) and the tautomers thereof.

Given the preceding formulas, it will be readily appreciated that the compounds of the present invention comprise either quinoxalines ($A_4$ is C and $A_5$ is N) and the corresponding quinoxalin-4-ones, or quinazolines ($A_4$ is N and $A_5$ is C) and the corresponding quinazolin-4-ones and quinazolin-5-ones. For any of the preceding compounds, $A_{1-3}$ may independently comprise C or N, provided at least one is a nitrogen, thereby including such compounds as imidazoles, pyrazoles, triazoles and tetrazoles. The compounds also include variants of the foregoing, such as tautomers.

$R_1$ and $R_2$ may each be independently selected from at least the groups indicated, and may appear at any of the available binding positions of the indicated six-member carbon ring. It is preferable, however, that at least one of $R_1$ and $R_2$ be other than hydrogen It is further preferred that the non-hydrogen substituent be an electron withdrawing group, as this appears to contribute to the activity of the compounds as EAA receptor antagonists. $R_3$ may appear on any carbon of the indicated ring, which carbon may be present at various positions depending on the compound.

In addition to the substituents specifically set forth, it is contemplated that other, non-interfering substituents may be present at available bonding sites. It can be readily determined if such additional constituents affect the use of a given compound for the purposes described herein. Therefore, such other compounds are equivalent to the compounds specifically identified by the structures (I) and (II), and fall within the scope of the present invention.

It will further be appreciated that various compounds of the present invention, while having similar utility, may have different selectivity when employed as EAA receptor antagonists, neuroprotective agents or the like. Selection of appropriate ones of these compounds for the various indications described herein is within the ordinary skill in the art based upon routine experimental procedure.

In addition to the compounds already discussed, the present invention includes the pharmaceutically acceptable salts of the compounds of formulas (I)–(IV). The forms which such salts may take are well understood in the art, and can include, for example, acid addition, or alkali metal or alkaline earth metal salts. Further discussion of the nature and formation of salts of this general type is provided in U.S. Pat. No. 4,902,695, issued to Ornstein on Feb. 20, 1990, the pertinent portions of which are hereby incorporated by reference.

All of the disclosed compounds of the present invention may be prepared in accordance with techniques known in the art, and as exemplified herein. The pharmaceutically acceptable salts are typically formed by reacting a compound of this invention with an equimolar or excess amount of salt forming reagent. The reactants are generally combined in a mutual solvent such as diethyl ether, benzene, ethanol or water and the salt normally precipitates out of solution within about one hour to ten days, and can be isolated by filtration.

Another aspect of the present invention is to provide pharmaceutical formulations comprising the EAA receptor antagonists of the present invention and a pharmaceutically acceptable carrier, diluent or excipient therefor The active ingredient will usually be mixed with a carrier, or diluted by a carrier, or enclosed within a carrier which may be in the form of a capsule, sachet, paper or other container. The active ingredient in such formulations preferably comprises 1–99% by weight of the formulation. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, ointments, gelatin capsules, suppositories, sterile injectable solutions and sterile packaged powders.

Suitable carriers, excipients and diluents for particular disclosed compounds may include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated to provide quick, sustained or delayed release of the active ingredient after administration to the patient by employing procedures well known in the art.

The compounds of this invention are useful as excitatory amino acid receptor antagonists. One embodiment of the present invention is a method for blocking one or more excitatory amino acid receptors in mammals which comprises administering to a mammal requiring decreased excitatory amino acid neurotransmission a pharmaceutically effective amount of a compound of the indicated formulas (I)–(IV). The term "pharmaceutically effective amount", as used herein, represents an amount of a compound of the invention which is capable of blocking one or more EAA receptors. The particular dose of compound administered will of course be determined by the particular circumstances surrounding the case, including the compound administered, the route of administration, the condition being treated and other typical considerations in the administration of pharmaceuticals. A typical daily dose will contain 1–500 mg/kg of the active compound, preferably 1–50 mg/kg. The compounds can be administered by a variety of routes including the oral, rectal, transdermal, subcutaneous, intravenous, intramuscular or intranasal routes.

A variety of physiologic functions have been shown to be subject to influence by excessive stimulation of EAA neurotransmission. As such, it is contemplated that the methods of the present invention include the treatment of a variety of disorders in mammals associated with this condition, which include neurological disorders such as epilepsy, stroke, brain and spinal cord trauma, cerebral ischaemia, muscular spasms, neurodegenerative diseases and conditions including Huntington's chorea and dementia of the Alzheimer's type, Parkinson's disease, and Amyotrophic lateral sclerosis, anxiety, urinary incontinence, analgesia, muscle spasms, opiate tolerance and withdrawal, and as an antipsychotic. The present invention therefore also provides methods of treating these disorders, as well as others which are linked to EAA receptor activity.

It is also an aspect of the present invention that the disclosed compounds operate as neuroprotective agents. By way of example, relatively low concentrations and brief exposures of neuronal cultures to at least certain endogenous EAA agonists, such as L-glutamate and L-aspartate, induce profound neuronal degeneration that can be prevented by EAA receptor antagonists. The efficient uptake of L-glutamate and L-aspartate into neuronal and glial cells after their neuronal release may be important as a protective mechanism to prevent the excessive stimulation of EAA receptors that leads to neuronal cell loss via excitotoxicity. It has been well established that excessive activation of ionotropic EAA receptors with NMDA, kainate, or AMPA produces neuronal excitotoxicity. This phenomena is discussed in detail in "Excitatory Amino Acid Receptor Antagonists as Potential Therapeutic Agents", by P. L. Ornstein and D. D. Schoepp, in Current CNS Patents, Vol. 1, No. 6, p. 1 et seq. (1990). It is therefore an aspect of the present invention to provide methods which comprise the administration of the disclosed compounds in a "neuroprotective amount", i.e. an amount effective to provide neuroprotection for EAA receptor(s) for which the compounds serve as antagonists.

The following examples further illustrate the compounds of the present invention and methods for their synthesis. The examples are not to be construed as limiting to the scope of the invention in any respect.

EXAMPLE I

Preparation of Triazoloquinoxaline Compounds

For purposes of demonstration, the following provides exemplary methodology for the preparation of triazoloquinoxaline compounds as contemplated by the present invention. These compounds each have the general formula:

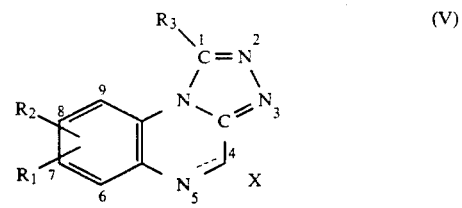

in which exemplary substituents $R_{1-3}$ are shown in Table I, with numerical references corresponding to those contained in the following text.

TABLE I[1]

| No. | $R_1$ | $R_2$ | $R_3$ | X |
|-----|-------|-------|-------|---|
| 1   | Cl    | Cl    | Methyl | H |
| 2   | Cl    | Cl    | Methyl | O |
| 3   | Cl    | Cl    | Ethyl  | H |
| 4   | Cl    | Cl    | Ethyl  | O |
| 5   | Cl    | Cl    | n-Propyl | H |
| 6   | Cl    | Cl    | n-Propyl | O |
| 7   | Cl    | Cl    | n-Butyl | H |
| 8   | Cl    | Cl    | n-Butyl | O |
| 9   | Cl    | Cl    | $CF_3$ | H |
| 10  | Cl    | Cl    | $CF_3$ | O |
| 11  | Cl    | Cl    | Phenyl | H |
| 12  | Cl    | Cl    | Phenyl | O |
| 12a | Cl    | Cl    | H      | O |
| 13  | F     | F     | H      | H |
| 14  | F     | F     | H      | O |
| 15  | H     | Br    | H      | H |
| 16  | $NO_2$ | H   | H      | H |
| 17  | $NO_2$ | H   | H      | O |
| 18  | $NO_2$ | $NO_2$ | H   | O |

[1] For these compounds, each $R_1$ was at the $C_7$ position, each $R_2$ was at the $C_8$ position, and each $R_3$ was at the $C_1$ position. When X is oxygen, it is attached at the $C_4$ position with a double bond.

A. Preparation of 2-Hydrazino-6,7-dichloroquinoxaline 4,5-Dichloro-1,2-phenylenediamine (25 g, 141.2 mmol) was suspended in 780 ml EtOH, and 13 g (142.0 mmol) of glyoxylic acid ($HO_2CCOH/H_2O$) was added. The mixture was heated at reflux for 3 hours, and then cooled and filtered, yielding 27.45 g of 6,7-dichloroquinoxalin-2-one as a solid. The product (25 g, 116.3 mmol) and 230 ml (911.7 mmol) of phosphorus oxychloride ($POCl_3$) were stirred at reflux (100° C.) for 3 hours. The mixture was cooled and ice/$H_2O$ added. The resulting brown/grey solid was filtered, and dried in an oven, yielding approximately 25 g of 2,6,7-trichloroquinoxaline To the 2,6,7-trichloroquinoxaline was added anhydrous EtOH (500 ml) to give a brown solution. 5.0 g (156 mmol) anhydrous hydrazine were added dropwise under $N_2$, turning the solution red immediately. The solution was heated at reflux for 1 hour, cooled and the resulting solid was collected. Recrystallization from 1500 ml 95% EtOH yielded 13.0 g of 2-hydrazino-6,7 dichloroquinoxaline B. Preparation of Exemplary Dichlorotriazole Compounds 1. Preparation of 1-Methyl-7,8-dichloro-1,2,4-triazolo[4,3-a]quinoxaline (1) and 1-Methyl-7,8-dichloro-1,2,4-triazolo[4,3-a]quinoxalin-4(5H)-one (2).

The hydrazino product (2.0 g, 8.7 mmol) of Example I.A. was combined with 18.4 g (113.5 mmol) triethylorthoacetate ($H_3CC(OEt)_3$) neat. The mixture was heated at reflux for 2 hours, cooled (adding EtOH), and filtered. The product was dried in an oven, and yielded 1.76 g of 1-methyl-7,8-dichloro-1,2,4-triazolo[4,3-a]quinoxaline (1).

The dichloro product (1) (500 mg; 1.97 mmol) was added to 16 ml HOAc, and then 5 ml of 30% $H_2O_2$ were added and the mixture warmed to 50° C. for 17 hours. The mixture was cooled to room temperature and filtered. The product was washed with water and dried in an oven at 50° C., 0.5 mm Hg, yielding 278 mg of 1-methyl-7,8-dichloro-1,2,4-triazolo[4,3-a]quinoxalin-4(5H)-one (2).

2. Preparation of 1-Ethyl-7,8-dichloro-1,2,4-triazolo [4,3 a]quinoxaline (3) and 1-Ethyl-7,8-dichloro-1,2,4triazolo-[4,3-a]quinoxalin-4(5H)-one (4).

The hydrazino compound (1.0 g, 4.36 mmol) of Example I.A. was combined with triethylorthopropionate ($H_3CCH_2C(OEt)_3$) and heated to 100° C. in an oil bath. The mixture was cooled to room temperature after 2½ hours, and EtOH was added with stirring. The resulting mixture was filtered and the product washed with EtOH and dried in an oven, yielding 830 mg of 1-ethyl-7,8 dichloro-1,2,4-triazolo[4,3-a]quinoxaline (3).

The triazole (3) (1.5 g, 5.64 mmol) was added to 47 ml of HOAc, and then 14 ml 30% $H_2O_2$ added. The mixture was warmed 4 hours at 50° C., then cooled to room temperature and poured into $H_2O$. The precipitate was filtered and dried, yielding 1.09 g of 1-ethyl-7,8-dichloro-1,2,4-triazolo[4,3-a]quinoxalin-4(5H)-one (4).

3. Preparation of 1-n-Propyl-7,8-dichloro-1,2,4-triazolo [4,3-a]quinoxaline (5) and 1-n-Propyl-7,8-dichloro-1,2,4-triazolo[4,3-a]quinoxalin-4(5H)-one (6).

The hydrazino compound (1.5 g, 6.5 mmol) of Example I.A. was combined with trimethylorthobutyrate and heated to 100° C. for 4½ hours. The reaction mixture was cooled to room temperature and the mixture was filtered and dried, yielding 1.10 g of 1-n-propyl-7,8-dichloro-1,2,4-triazolo[4,3-a]quinoxaline (5).

800 mg (2.8 mmol) of the prior quinoxaline compound (5) were added to 22.5 ml of HOAc, and then 7 ml of 30% $H_2O_2$ were added and the reaction mixture warmed to 50° C. for 16 hours. The resulting mixture was cooled to room temperature and the product filtered and dried, yielding 280 mg of 1-n-propyl-7,8-dichloro-1,2,4-triazolo[4,3-a]quinoxalin-4(5H)-one (6).

4. Preparation of 1-n-Butyl-7,8-dichloro-1,2,4-triazolo [4,3-a]quinoxaline (7) and 1-n-Butyl-7,8-dichloro-1,2,4-triazolo[4,3-a]quinoxalin-4(5H)-one (8).

The hydrazino compound (2.0 g, 8.7 mmol) of Example I.A. was combined with 18.4 g (113.1 mmol) trimethylorthovalerate and heated to 100° C. for 2 hours. The reaction mixture was cooled to room temperature, and then filtered and washed with EtOH and the product dried, yielding 1.37 g of 1-n-butyl-7,8-dichloro-1,2,4-triazolo[4,3-a]quinoxaline (7).

The carbonyl compound was prepared by combining 500 mg (1.7 mmol) of the quinoxaline compound (7) and 16 nil HOAc, and then adding 5 ml of 30% $H_2O_2$. The mixture was heated to 60° C. for 16 hours, and then cooled. The product was recovered by filtration and dried at 0.5 mm and 60° C. overnight, yielding 150 mg of 1-n-butyl-7,8-dichloro-1,2,4-triazolo[4,3-a]quinoxalin-4(5H)-one (8).

5. Preparation of 1-Trifluoromethyl-7,8-dichloro-1,2,4-triazolo[4,3-a]quinoxaline (9) and 1-Trifluoromethyl-7,8-dichloro-1,2,4-triazolo[4,3-a]quinoxalin-4(5H)-one (10).

The hydrazino compound (1.0 g, 4.4 mmol) of Example I A. was added to 5 ml (29.0 mmol) of ice-cold trifluoroacetic acid. The reaction mixture was heated to 100° C. for 3 hours and poured over ice/$H_2O$. The resulting solution went from dark brown to a yellow precipitate. Filtering and washing with water yielded 950 mg of 1-trifluoromethyl-7,8-dichloro-1,2,4-triazolo[4,3-a]quinoxaline (9).

800 mg (2.3 mmol) of the quinoxaline (9) was stirred in 22 ml HOAc, and 7 ml of 30% $H_2O_2$ was added. The reaction mixture was heated to 55° C. for 16 hours, and then cooled to room temperature. Filtering and drying the product yielded 330 mg of 1-trifluoromethyl-7,8-dichloro-1,2,4-triazolo [4,3-a]quinoxalin-4(5H)-one (10).

6. Preparation of 1-Phenyl-7,8-dichloro-1,2,4-triazolo [4,3-a]quinoxaline (11) and 1-Phenyl-7,8-dichloro-1,2,4-triazolo[4,3-a]quinoxalin-4(5H)-one (12).

The hydrazino compound of Example I.A. was combined with triethylorthobenzoate and heated to approximately 100° C. in an oil bath. The material became a soft solid and would not stir, and was allowed to sit in the 100° C. oil bath for 3 hours It was then cooled to room temperature and EtOH was added with stirring. The solid product was filtered and dried in an oven, yielding 702 mg. This product was then stirred for 1 hour in EtOH and filtered, yielding 445 mg of product, which was recrystallized from EtOH and $CHCl_3$, providing 246 mg of 1-phenyl-7,8-dichloro-1,2,4-triazolo[4,3-a]quinoxaline (11).

The triazole (11) (1.5 g, 4.7 mmol) was added to acetic acid (37 ml). $H_2O_2$ (10 ml, 30%) was added and the mixture warmed for 4 hours at 50° C. The mixture was then cooled to room temperature, poured into $H_2O$, and filtered. Upon drying in an oven, recrystallizing from DMF and drying, there was recovered 120 mg of 1-Phenyl-7,8-dichloro-1,2,4-triazolo[4,3-a]quinoxalin-4(5H)-one (12). In a similar fashion, various other dichloroquinoxalinones can be readily prepared, including for example 7,8-dichloro-1,2,4-triazolo[4,3-a]quinoxalin-4(5H)-one (12a).

C. Preparation of Difluorotriazolo Compounds (13-14)

The foregoing methodology was followed starting with 2-chloro-6,7-difluoroquinoxaline. This compound (4.00 g, 19.9 mmol) was dissolved in 100 ml of absolute EtOH. Hydrazine (1.4 ml, 44 mmol) was added, and the mixture heated at reflux for 2½ hours. The mixture was cooled and allowed to stand overnight before collecting the resulting precipitate, yielding 3.80 g of an orange, solid 2-hydrazino-6,7-difluoroquinoxaline. This product (3.8 g, 19.4 mmol) was stirred in 30 ml triethylorthoformate and heated at reflux (100° C.) for 5 hours. The resulting product was cooled to room temperature, filtered and dried, yielding 2.63 g of 7,8-difluoro-1,2,4-triazolo[4,3-a]quinoxaline (13).

The difluoro compound (13) (1.81 g 8.78 mmol) was added to glacial AcOH (25 ml) and treated with 80% monoperoxyphthalic acid Mg salt.$6H_2O$ (2.88 g, 4.66 mmol). The mixture was heated at 60°-70° C. overnight and initially went into solution, then a precipitate formed after 1-2 hours. This was allowed to cool, before pouring onto $H_2O$. The precipitate was collected by filtration and air dried to yield 7,8-difluoro-1,2,4-triazolo[4,3-a]quinoxalin-4(5H)-one (14).

D. Preparation of meta-Dichlorotriazolo Compound (14a)

3,5-Dichloro-1,2-phenylenediamine (5.00 g, 28.2 mmol) and glyoxalic acid ($HO_2CCOH/H_2O$) were combined in 120 ml of abs EtOH. The mixture was heated at reflux for 18 hours, allowed to cool, then filtered to yield 3.00 g (50%) of an approximately 7:1 mixture of 6,8-dichloroquinoxalin-2-one and 5,7-dichloroquinoxalin-2-one, respectively. The regioisomeric mixture (2.98 g, 13.9 mmol) and POCl₃ were stirred at reflux for 2.5 hours. The mixture was cooled, poured slowly onto H₂O, and the precipitate collected to give 3.18 g (98%) of a mixture of 2,6,8-trichloroquinoxaline and 2,5,7-trichloroquinoxaline. This material was passed through a silica flash chromatography column eluting with 10% EtOAc / hexane without resolving the two regioisomers.

The trichloroquinoxalines (1.40 g, 6.00 mmol) were treated with hydrazine (0.5 ml, 16 mmol) at reflux for 3 hours, allowed to cool, and the precipitate collected. This regioisomeric product mixture was heated in triethylorthoformate (15 ml) at 100° for 5 hours. The mixture was allowed to cool, diluted with Et₂O, and 0.96 g (65%) of an approximately 8:1 mixture of 7,9-dichloro-1,2,4-triazolo[4,3 a]quinoxaline and 6,8-dichloro 1,2,4-triazolo[4,3-a]quinoxaline, respectively, was collected. This mixture (0.820 g, 3.43 mmol) was treated with 80% monoperoxyphthalic acid Mg salt.6H₂O (1.70 g, 2.75 mmol) in 20 ml of glacial AcOH at 60°-70° as previously described. After cooling, the mixture was poured onto 300 ml of H₂O and 0.467 g (87%) of a yellow precipitate collected. Recrystallization from MeOH afforded 0.200 g of 7,9-dichloro-1,2,4-triazolo[4,3a]-quinoxalin-4(5H)-one (14a) which contained 2% or less of the 6,8-dichloro isomer.

E. Preparation of Bromotriazolo Compound (15)

Quinoxalin-2-one (2-hydroxyquinoxaline) (14.62 g, 100 mmol) was added to glacial AcOH (700 ml) and treated with bromine (5.4 ml, 105 mmol in 1 ml AcOH) added dropwise over 15 minutes, yielding 7-bromoquinoxalin-2-one. The reaction mixture was diluted with 750 ml of H₂O and 50 ml of 1 N Na₂S₂O₃ and the precipitate was collected by filtration to give 13.7 g of a tan solid. This compound (1.00 g, 4.46 mmol) was added to 30 ml of POCl₃ and warmed to reflux for 1 hour. The mixture darkened and became homogeneous. Upon cooling, the mixture was poured slowly onto 300 ml of H₂O, and the resultant solid collected by filtration. This 2-chloro product (0.90 g, 3.7 mmol) was added to abs EL OH (30 ml) and treated with anhydrous hydrazine (0.30 ml, 9.4 mmol). The mixture was heated at reflux under N₂ for 3 hours. Upon cooling, a precipitate formed. The solution was cooled further in an ice bath before collecting the resultant brown crystals. The hydrazino compound (0.67 g, 2.80 mmol) was added to 20 ml of triethylorthoformate and the suspension heated at 100° C. under N₂ for 5 hours. The remaining precipitate was collected by filtration, washed with Et₂O and air-dried, yielding 8-bromo-1,2,4-triazolo[4,3-a]quinoxaline (15).

F. Preparation of Nitrotriazoloquinoxaline Compounds (16–18)

The procedure of Example I.D. was followed except the quinoxalin-2-one was converted to the 6-nitroquinoxalin-2-one by first dissolving in conc. H₂SO₄ and cooling in an ice bath, and adding KNO₃ in 3 portions. The product was collected by conventional technique and subsequently converted to 2-hydrazino-6-nitroquinoxaline. This compound was reacted with triethylorthoformate as per Example I.D., yielding 7-nitro-1,2,4-triazolo[4,3-a]quinoxaline (16).

The foregoing triazole (16) was suspended in HOAC, and 30% H₂O₂ was added dropwise. The reaction was heated to 60° C. for 16 hours under N₂, and then cooled to room temperature. Upon filtering a yellow solid 7-nitro-1,2,4-triazolo[4,3-a]quinoxalin-4(5H)-one (17) was recovered.

This product (17) was dissolved in H₂SO₄ and cooled in an ice/H₂O bath. KNO₃ was added and the ice bath removed. The solution was stirred an additional 2 hours and then heated at 50° C. for 40 hours, yielding 7,8-dinitro 1,2,4-triazolo[4,3-a]quinoxalin-4(5H) one (18).

It will be appreciated that by similar preparatory techniques within the skill in the art a variety of other triazoloquinoxaline compounds may be obtained. Prepared in accordance with known techniques are triazoloquinoxalines and triazoloquinoxalinones in which the substituents are independently selected from those previously defined for R₁, R₂, and R₃.

EXAMPLE II

Preparation of Tetrazoloquinoxaline Compounds

In this example, the preparations are indicated for exemplary tetrazoloquinoxaline compounds as contemplated by the present invention. These compounds each have the general formula:

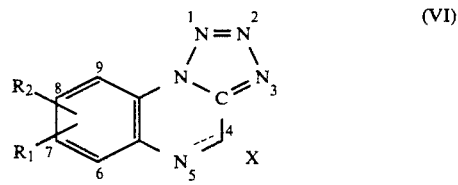

in which the substituents R₁₋₃ and X are shown in Table II, with numerical references corresponding to those contained in the following text.

TABLE II[2]

| No. | R₁ | R₂ | X |
|-----|-----|-----|---|
| 19 | H | H | H |
| 20 | H | H | O |
| 21 | H | Br | O |
| 22 | H | NO₂ | O |
| 23 | NO₂ | H | H |
| 24 | NO₂ | H | O |
| 25 | NO₂ | NO₂ | O |
| 26 | F | N₃ | H |
| 27 | F | N₃ | O |
| 27a | Cl | Cl | O |

[2]Each R₁ was at the C₇ position, and each R₂ was at the C₈ position. When X is oxygen, it is attached at the C₄ position with a double bond.

A. Preparation of Tetrazolo[1,5-a]quinoxaline (19) and Tetrazolo[1,5-a]quinoxalin-4(5H)-one (20)

Quinoxalin-2-one (14.62 g, 100 mmol) was added to POCl₃ (100 g, 0.65 mmol) and the mixture heated at reflux for 1.5 hours under N₂. Upon cooling, the mixture was poured slowly, portionwise onto 700 ml of H₂O. The black solution was extracted with CH₂Cl₂ (2×250 ml). The combined CH₂Cl₂ portions were washed with H₂O, dried over Na₂SO₄, filtered, and evaporated to give a brown, solid 2-chloroquinoxaline. A portion of said product (4.00 g, 24.3 mmol) was combined with 5 ml of 1 N HCl, and NaN₃ (1.89 g, 29.1 mmol) in 220 ml of abs EtOH and heated at reflux for 7 hours. The mixture was allowed to cool overnight, which led to precipitation of yellow-brown needles of tetrazolo[1,5-a]quinoxaline (19).

The tetrazoloquinoxaline (19) (2.50 g, 14.6 mmol) was added to 40 ml of glacial acetic acid, followed by addition of 15 ml of 30% $H_2O_2$. The mixture was warmed to 50°-60° C. for 4 hours. An additional 5-10 ml AcOH was required to facilitate complete dissolution. Additional $H_2O_2$ (10 ml) was added, and the reaction allowed to continue for 12 hours at 80° C. Upon cooling, a precipitate resulted which was diluted further with $H_2O$ before collecting by filtration, washing with $H_2O$, and air drying to give 1.72 g of a cream solid tetrazolo[1,5-a]quinoxalin-4(5H)-one (20).

B. Preparation of 8-Substituted Tetrazolo[1,5-a]quinoxalin-4(5H)-ones

The tetrazoloquinoxalinone (20) of Example II.A. (0.150 g, 0.801 mmol) and $Ag_2SO_4$ (0.25 g, 0.80 mmol) were added to 5 ml of conc. $H_2SO_4$. Bromine (0.06 ml, 1.2 mmol) was added and the mixture stirred at 23° C. for 47 hours. The mixture was filtered through a sintered glass funnel, washed with $H_2O$, and air-dried to give 0.158 g of a tan solid. Recrystallization from DMF/$H_2O$ afforded 0.138 g of a tan crystalline product, 8-bromotetrazolo[1,5-a]quinoxalin-4(5H)-one (21).

In an alternate procedure, the tetrazoloquinoxalin-4-one (20) of Example II.A. (0.510 g, 2.72 mmol) was added to 15 ml of conc. $H_2SO_4$. $KNO_3$ (0.83 g, 8.2 mmol) was added, and the mixture stirred at 23° C. for 4 hours. The mixture was poured onto ice-$H_2O$ (100 ml) which led to formation of a yellow precipitate. Recrystallization from 10 ml of 50% aqueous DMF gave 0.361 g of a beige solid 8-nitrotetrazolo[1,5-a]quinoxalin-4(5H)-one (22).

C. Preparation of 7-Nitrotetrazole Compounds.

$KNO_3$ (7.35 g, 0.0727 mmol) was added in three portions to a solution of quinoxalin-2-one (10.62 g, 72.7 mmol) in conc. $H_2SO_4$ (120 ml) maintained in an ice bath. The ice bath was removed, and the mixture allowed to stir for 2½ hours longer, and then poured onto 1 liter of ice-$H_2O$ to cause precipitation of a yellow solid. The mixture stood overnight before collecting the precipitate by filtration, washing with $H_2O$, and air drying to yield 9.97 g of a yellow solid. This 6-nitroquinoxalin-2-one (3.00 g, 15.7 mmol) was heated at reflux in $POCl_3$ ml) and $PCl_5$ (6.0 g) under $N_2$ for 3½ hours. Upon cooling, the mixture was poured onto $H_2O$, adding ice as necessary to cool the resultant exotherm. The resulting crystals were collected by filtration, washed with $H_2O$, and air-dried to yield 3.00 g of yellow needles comprising 2-chloro-6-nitroquinoxaline.

The 2-chloro-6-nitroquinoxaline (3.00 g, 14.3 mmol), 5 ml of 1 N HCl, and $NaN_3$ (1.12 g, 17.2 mmol) were combined in 60 ml of absolute EtOH, and heated at reflux for 17 hours. A precipitate remained throughout The product was collected by filtration, and air-dried to give 3.8 g of a tan solid. The product was slurried in $H_2O$ and recollected to yield 2.75 g of a light brown solid. Recrystallization from 15 ml of 2:1 DMF/$H_2O$ gave 0.793 g of tan-brown crystals of 7-nitrotetrazolo[1,5-a]quinoxaline (23).

The nitrotetrazoloquinoxaline (23) (1.84 g, 8.51 mmol) was added to a mixture of 15 ml of glacial AcOH and 20 ml of 30% $H_2O_2$ and heated at 85° C. in an oil bath for 16 hours. Upon cooling, the mixture was diluted with $H_2O$ (50 ml) and the precipitate collected by filtration. Recrystallization from 40 ml of 50% aq. DMF gave 1.29 g of yellow flocculant needles comprising 7-nitrotetrazolo[1,5-a]quinoxalin-4(5H)-one (24). This nitrotetrazoloquinoxalinone (3.00 g, 12.9 mmol) was added to conc. $H_2SO_4$ (40 ml) and treated with $KNO_3$ (1.43 g, 14.1 mmol) with warming to 50° C. under $N_2$. The mixture was poured onto 600 ml of ice-$H_2O$, and a light yellow solid collected by filtration and washed with $H_2O$, yielding 7,8-dinitrotetrazolo[1,5-a]quinoxalin-4(5H)-one (25).

D. Preparation of 8-Azido-7-fluorotetrazoles 4,5-Difluoro-2-nitroaniline (20.00 g, 115 mmol) was catalytically hydrogenated by $H_2$ in 275 ml EtOH over 10% Pd/C at room temperature for 4 hours. The mixture was filtered to remove Pd/C, and EtOH was removed in vacuo to afford 14.63 g of a dark green solid difluorophenylenediamine. This compound (14.48 g, 100 mmol) was combined with glyoxalic acid hydrate (11.97 g, 130 mmol) in 250 ml of absolute EtOH and heated at reflux under $N_2$ for 20 hours. Upon cooling and standing for 24 hours, the resultant purple solid was collected by filtration, yielding 14.6 g of 6,7-difluoroquinoxalin-2-one.

The difluoroquinoxalinone (10.00 g, 54.9 mmol) was heated at reflux in $POCl_3$ (125 g, 800 mmol) under $N_2$ for 3 hours. The mixture was allowed to stand overnight at room temperature before carefully pouring onto 1.2 liters of $H_2O$. A nearly black precipitate resulted which was collected, washed with $H_2O$, and air-dried to yield 16.72 g. The solid was taken up in 400 ml of $CH_2Cl_2$, filtered to remove insoluble black residue, and the filtrate evaporated to give a salmon solid (8.77 g). This material, 2-chloro-6,7-difluoroquinoxaline (4.37 g 21.8 mmol), was added to 120 ml of abs EtOH containing 5 ml of 1 N HCl. Sodium azide (2.1 g, 32 mmol) was added, and the mixture heated at reflux under $N_2$ for 18 hours. Upon cooling, the resulting brown needles were collected by filtration, washed with EtOH, and air-dried, to give 3.71 g of 7-fluoro-8-azidotetrazoloquinoxaline (26).

The fluoroazidotetrazoloquinoxaline (26) (2.00 g, 8.69 mmol) was added to glacial acetic acid. Excess monoperoxyphthalic acid, Mg salt hexahydrate was added as needed and the suspension was heated at 60°-70° C. until the reaction was complete. The reaction mixture was poured onto $H_2O$ and stirred, yielding a pink precipitate which was collected, washed with $H_2O$, and air-dried. Recrystallization from 20 ml of DMF/$H_2O$ (minimal $H_2O$) gave a salmon pink solid. The solid was resuspended in $H_2O$ and MeOH, and air-dried, giving the product 7-fluoro-8-azidotetrazoloquinoxalin-4(5H)-one (27).

It will be appreciated that by similar preparatory techniques within the skill in the art a variety of other tetrazoloquinoxaline compounds may be obtained. Prepared in accordance with known techniques are tetrazoloquinoxalines and tetrazoloquinoxalinones in which the substituents are independently selected from those previously defined for $R_1$, $R_2$, and $R_3$. For example, in a similar fashion is prepared 7,8-dichlorotetrazolo[1,5-a]quinoxalin-4(5H)-one (27a).

EXAMPLE III

Preparation of Pyrazolo[1,5-c]quinazolinones

For purposes of demonstration, the following provides methodology for the preparation of exemplary pyrazoloquinazolinone compounds as contemplated by the present invention. These compounds each have the general formula:

$$\text{(VII)}$$

in which the substituents $R_{1-3}$ are shown in Table III, with numerical references corresponding to those contained in the following text.

TABLE III[3]

| No. | $R_1$ | $R_2$ | $R_3$ |
|-----|-------|-------|-------|
| 28 | H | Br (9) | H |
| 29 | H | Cl (9) | H |
| 30 | Cl (7) | H | H |
| 31 | Cl (8) | H | H |
| 32 | Cl (8) | Cl (9) | H |
| 33 | Cl (7) | Cl (9) | H |
| 34 | H | H | $CH_3$ (2) |
| 35 | H | $CF_3$ (8) | H |

[3] The C position for each substituent is shown in parentheses.

The following syntheses are based upon the preparation of the pyrazolo[1,5-c]quinazolinones by ring closure of a 3-(2-aminophenyl)pyrazole. This synthesis is generally discussed in G. Alberti, "Gazz. Chim. Ital.", vol. 87, p. 772 (1957).

A. Preparation of 9-Bromopyrazolo[1,5-c]quinazolin-5(6H)-one 17.02 g (100 mmol) of 4-bromoaniline were dissolved in 150 MeOH and 15.63 g (110 mmol) of dimethylacetylenedicarboxylate were added and stirred at room temperature for 11 days. Upon evaporation, green crystals formed which were taken up in 50 ml of diphenyl ether and added dropwise over five minutes to 100 ml diphenyl ether at 250° C.. The mixture was allowed to set at 250° C. for 20 minutes, and then cooled to room temperature. It was then diluted with petroleum ether, filtered and resuspended in petroleum ether. The remaining crystals were filtered and dried, yielding 10.38 g (37 mmol) of a 6-bromokynurenate product. 8.38 g (30 mmol) of the 6-bromokynurenate were slurried into a 200 ml solution of NaOH and stirred at room temperature. The reaction mixture was filtered and the filtrate was extracted twice with equal amounts of EtOAc and twice with equal amounts of methylene chloride. Acidification to pH 2 by addition of concentrated HCl, followed by filtering and air drying, yielded 2-carboxy-4-hydroxy-6-bromoquinoline.

The 2-carboxy-4-hydroxy-6-bromoquinoline (5.42 g, 20 mmol) was slurried in 250 ml of light mineral oil and heated to 270°-295° C. for 10-15 minutes. The mixture was allowed to cool overnight, diluted with chloroform and filtered, and then washed with adequate amounts of chloroform, yielding 6-bromo-4-hydroxyquinoline.

The bromohydroxyquinoline (1.97 g, 8.79 mmol) was dissolved in 21 ml of ethylene glycol and hydrazine hydrat (4.2 ml) was added. To this mixture were added 1.3 g (12.2 mmol) of hydrazine dihydrochloride, and the resulting mixture was heated to reflux and stirred under nitrogen. The resulting material was poured onto 300 ml of $H_2O$. The mixture was extracted with $CH_2Cl_2$, basified with $NaHCO_3$ and extracted further with $CH_2Cl_2$. The combined organic portions were washed with water, dried over $Na_2SO_4$, filtered, and concentrated in vacuo to give a brown oil, yielding bromoanilinopyrazole (i.e., 3-(2-amino-5-bromophenyl)pyrazole).

The bromoanilinopyrazole (0.73 g, 3.07 mmol) was added to 25 ml of THF. Triphosgene (1.09 g, 3.67 mmol) was added, followed by $K_2CO_3$ (0.64 g, 4.63 mmol), and the suspension which resulted was heated at reflux for 20 hours. Upon cooling, the mixture was carefully diluted with $H_2O$, and the remaining precipitate collected by filtration. Recrystallization from MeOH yielded cottony white crystals of 9-bromopyrazolo[1,5-c]quinazolin-5(6H)-one (28).

B. Preparation of 9-Chloropyrazolo[1,5-c]quinazolin-5(6H) one (29)

6-Chloro-4-hydroxyquinoline was prepared in a manner similar to that described in Example III.A.

C. Preparation of 7-Chloropyrazolo[1,5-c]quinazolin-5(6H)-one (30)

In the manner of Examples III.A. and B., 8-chloro-4-hydroxyquinoline was prepared from 2-chloroaniline and dimethyl acetylenedicarboxylate.

D. Preparation of 8-Chloropyrazolo[1,5-c]quinazolin-5(6H)-one (31) and 8,9-Dichloropyrazolo[1,5-c]quinazolin-5(6H)-one (32)

In the manner of Examples III.A. and B., 8-chloropyrazolo[1,5-c]quinazolin-5(6H)-one (31) was prepared.

The 8-chloropyrazoloquinazolinone (31) (1.00 g, 4.55 mmol) was added to glacial AcOH (20 ml) and treated with sulfuryl chloride (0.78 ml, 6.7 mmol). The mixture was heated at 75°-85° C. for six hours. Additional $SO_2Cl_2$ was added and the reaction allowed to continue overnight. Upon cooling, the mixture was poured onto 80 ml of $H_2O$ and the resulting precipitate collected, washed with $H_2O$ and air dried. Upon recrystallation from DMF (150 ml) and drying in a vacuum oven at 75° C. for 23 hours, there were recovered white crystals of 8,9-dichloropyrazolo[1,5-c]quinazolin-5(6H)-one (32).

E. Preparation of 7,9-Dichloropyrazolo[1,5-c]quinazolin-5(6H)-one (33)

In the manner of Examples III.A. and B., 7,9-dichlo,opyrazolo[1,5-c]quinazolin-5(6H)-one (33) was prepared.

F. Preparation of Analogous Pyrazoles

In accordance with the previously described procedures, a variety of additional compounds are prepared. For example, the combination of anilinomethylpyrazole (2.856 g, 16.5 mmol) with 100 ml of THF, and subsequent addition of triphosgene (5.63 g, 19.0 mmol) and $K_2CO_3$ (3.28 g, 23.7 mmol) followed by heating at reflux for 24 hours, cooling, and quenching and diluting with an equal volume of $H_2O$, yielded upon recrystallization 0.633 g of white crystalline 2-methylpyrazolo[1,5-c]quinazolin-5(6H)-one (34).

In similar fashion is prepared the compound 8-trifluoromethylpyrazolo[1,5-c]quinazolin-5(6H)-one (35).

EXAMPLE IV

Preparation of Imidazole Compounds

The following provides methodology for the preparation of exemplary imidazole compounds as contemplated by the present invention.

2,6,7-Trichloroquinoxaline (10.00 g, 42.8 mmol) and Et$_2$N (7.7 ml, 55 mmol) were combined in 200 ml of toluene Aminoacetaldehyde dimethylacetal (6.1 ml, 56 mmol) was added, and the mixture heated at reflux for 22 hours. The mixture was filtered to remove Et$_3$N-HCl, the salts were collected and washed with EtOAc, and the filtrate concentrated in vacuo to give a dark oil. Flash chromatography was performed on a 100 mm column packed with 5 in. silica and eluted with 45% EtOAc/hexane. 100 ml fractions were collected, and fractions 16–35 contained 8.55 g of a deep red oil which was azeotroped with ether and dried.

The resulting acetal (7.50 g, 24.8 mmol) was added to MeOH (100 ml) and concentrated HCl (20 ml), and heated at reflux for 6 hours. After standing at room temperature, 2 ml concentrated HCl were added, and the mixture was refluxed for 6 hours longer. The mixture was concentrated in vacuo. The residue was neutralized by the addition of diluted NaHCO$_3$, and the mixture was then stirred overnight, with a brown solid being collected by filtration and washed with H$_2$O and air-dried to give 4.23 g of 7,8-dichloroimidazo[1,2-a]quinoxaline (36).

The imidazoquinoxaline (1.20 g, 5.04 mmol) was added to 20 ml of glacial acetic acid, treated with 80% MMPP (3.00 g, 4.85 mmol) and heated at 55° C. for 18 hours. Additional MMPP (1.00 g, 1.62 mmol) was added and the reaction allowed to continue for 24 hours longer. Additional portions of MMPP (1.00 g, 1.62 mmol) were added, and the reaction allowed to continue for several days. The mixture was poured onto 400 ml of H$_2$O, stirred for one hour, and the precipitate was collected by filtration and washed with H$_2$O, yielding a dark yellow solid 7,8-dichloroimidazo[1,2-a]quinoxalin-4(5H)-one (37).

In another procedure, anilinobenzimidazole (i.e., 2-(2-amino-5-chlorophenyl)benzimidazole) (1.30g, 5.33 mmol) was dissolved in 120 ml of THF. Triphosgene (1.74g, 5.86 mmol) was added, followed by K$_2$CO$_3$ (0.884 g, 6.40 mmol). The resultant suspension was heated at reflux for 24 hours. TLC (50% EtOAc/hexane) showed starting material remained Additional triphosgene (0.34g, 1.1 mmol) and K$_2$CO$_3$ were added, and the reaction allowed to continue for a total of 44 hours. The mixture was diluted with H$_2$O (approximately 350 ml), and the resulting precipitate collected by filtration, washed with water, and air dried to yield 1.47 g of a gray solid. This solid was recrystallized from DMF/H$_2$O to yield gray crystals of the chlorobenzimidazo[1,2-a]quinazolin-4(5H)-one (38):

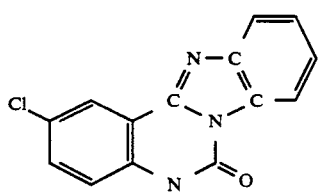

(VIII)

Similar preparatory techniques within the skill in the art permit the preparation of the variety of other compounds disclosed herein. Such compounds include quinoxalines and the corresponding quinoxalin-4-ones, or quinazolines and the corresponding quinazolin-4-ones and quinazolin-5-ones, and such compounds as imidazoles, pyrazoles, triazoles and tetrazoles. Similarly, the compounds may be prepared with the various substituents as previously defined for R$_{1-3}$ and X.

Activity as EAA Receptor Antagonists

The disclosed compounds have been found to be useful as EAA antagonists and as neuroprotective agents. Referring to Table IV, there are shown the results obtained in testing a representative number of these compounds. In Table IV, the activity of the compounds for EAA receptor binding is indicated. Compounds were evaluated for their ability to displace [$^3$H]-CGS191755, [$^3$H]-glycine, [$^3$H]-AMPA and [$^3$H]-kainate at a screening concentration of 10 µM.

TABLE IV

| | EAA RECEPTOR BINDING | | |
|---|---|---|---|
| Compound | [$^3$H]-Glycine Binding % DSPL10 @ 10 uM | AMPA % DSPL @ 10 uM | KA % DSPL @ 10 uM |
| (1) | 0 | 35.1 | 16.8 |
| (2) | 18 | 78.3 | 28.0 |
| | | 75.1 | |
| (3) | 63 | 7.9 | 12.0 |
| (4) | 53 | 55.1 | 21.4 |
| | | 52.3 | |
| (5) | 2 | −1.6 | 3.9 |
| (6) | 75 | 77.1 | 32.1 |
| | | 85.6 | |
| (7) | −2 | 4.2 | −6.4 |
| (8) | 60 | 64.6 | 33.8 |
| | | 1.1 | |
| (9) | −6 | | |
| (10) | 40 | 56.8 | 12.5 |
| | | 38.5 | |
| (11) | −3 | 1.7 | 9.1 |
| (12) | −1 | 3.6 | 8.2 |
| (12a) | 79 | 64.3 | |
| | 42 | 67.9 | |
| (14a) | 87 | | |
| (15) | −3 | 1.6 | −4.3 |
| (16) | −5 | 1.7 | 3.0 |
| (17) | 52 | 85.1 | 34.7 |
| | | 77.4 | |
| (18) | 50 | 77.4 | 15.6 |
| | | 55.0 | |
| (21) | 6 | 10.2 | 30.8 |
| (22) | 0 | 0.7 | 0.5 |
| (23) | −1 | 1.0 | −3.8 |
| (24) | 2 | 38.4 | 2.8 |
| (25) | 3 | 11.0 | 0.4 |
| | | −1.6 | −2.1 |
| (26) | −2 | −1.8 | 5.5 |
| (27) | 5 | 1.7 | 2.5 |
| (27a) | 37 | 38 | |
| (28) | 4 | 20.7 | 2.6 |
| (29) | 5 | 23.1 | 0.3 |
| (30) | 0 | 14.8 | −0.4 |
| (31) | 42 | 46 | 11.5 |
| (32) | | 4.9 | −0.1 |
| | | 9.3 | |
| (33) | −3 | 5.1 | 7.4 |
| (34) | 13 | 0.2 | 0.9 |
| (35) | 51 | 54.8 | 8.4 |
| (36) | 88 | 53.3 | 23.6 |
| (38) | 3 | 4.1 | −0.8 |

EAA Receptor Binding

Binding assays, except for glycine binding, were performed in accordance with the methods described in Schoepp et al., J. Pharmacology and Exp. Therap., Vol.

255, No. 3, pp. 1301-1308 (1990). For all binding assays, male Sprague-Dawley rats (150-175 g) were used. Displacement of the specific binding of [$^3$H]CGS19755 (10 nM) to Triton-X-treated synaptosomal membranes of rat forebrain was used to determine NMDA receptor affinity. Nonspecific binding was determined using 10 μM L-glutamate. Samples were incubated in an ice bath for 30 minutes, and bound ligand was separated from the free ligand by rapid filtration through Whatman GF/B glass fiber filters.

The binding of [$^3$H]AMPA (5 nM) was conducted with crude membranes of rat forebrain in the presence of 100 mM KSCN, as described by Nielsen et al., "Studies on Receptor-Active Conformations of Excitatory Amino Acid Agonists and Antagonists," Eur. J. Med. Chem. Chim. Ther. 21:433-437 (1986). Nonspecific binding was determined with 10 μM nonlabeled AMPA.

[$^3$H]Kainate binding was performed using washed synaptosomal membranes from the rat forebrain, prepared as described by Simon et al., "Binding of [$^3$H]Kainic Acid, an Analogue of L-Glutamate, to Brain Membranes," J. Neurochem. 26:141-147 (1976). [$^3$H]Kainate (5 nM) was added to 50 mM Tris-HCl buffer (pH 7.4 at 4°) containing 200-300 μg/ml of tissue protein. Samples were incubated for 30 minutes in an ice bath and then rapidly filtered using a Brandel cell harvester and Whatman GF/C filters. Filters were washed twice with 3 ml of cold buffer. Nonspecific binding was determined using 100 μM nonlabeled kainate.

The compounds were examined for their ability to displace [$^3$H]-glycine from washed membranes of rat brain cortex according to the methods of Shinohara et al., "Ontogeny of Strychnine-Insensitive [$^3$H]Glycine Binding Sites in Rat Forebrain", Neurosci. Lett. 105 (1990) 307-311. In each assay, 10 nmol [$^3$H]-glycine and 25 μg tissue were incubated with test compounds (10 μM in a total volume of 0.5 ml for 60 minutes on ice; incubations were terminated by centrifugation. Nonspecific binding was defined as that remaining in the presence of 10 μM D-serine.

The foregoing test results presented in Table IV demonstrate the utility of the described compounds as inhibitors of EAA receptor ligands of the EAA receptors.

While the invention has been described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A method for blocking one or more excitatory amino acid receptors in a mammal requiring decreased excitatory amino acid neurotransmission which comprises administering to the mammal a pharmaceutically effective amount of a compound of the general structure

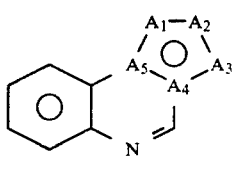

(I)

or

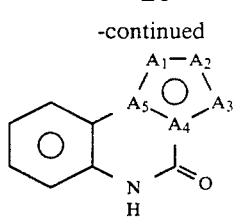

(II)

a tautomer thereof, or a pharmaceutically acceptable salt thereof, in which
each of $A_1$, $A_2$ and $A_3$ is independently either C or N except that at least one of $A_1$, $A_2$ and $A_3$ is N; and $A_4$ is C and $A_5$ is N.

2. The method of claim 1 which the compound is a tetrazolo[1,5-a]quinoxalin-4-one.

3. The method of claim 1 and which comprises administering a compound selected from the group consisting of:

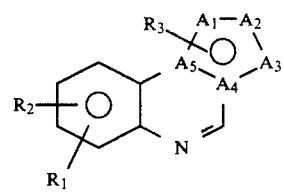

(III)

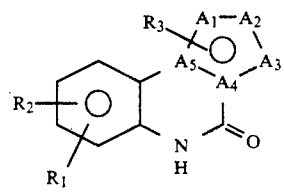

(IV)

a tautomer thereof, and a pharmaceutically acceptable salt thereof, in which:
$A_{1-5}$ are as previously defined;
each of $R_1$ and $R_2$ is independently hydrogen, halogen, CN, $NO_2$, $C_1$-$C_4$ alkyl, phenyl or fused benzo, azido, $CF_3$, $NHSO_2R'$ with $R'$ comprising $C_1$-$C_4$ alkyl or phenyl, or $SO_2NR''R'''$ with each of $R''$ and $R'''$ being either H or a $C_1$-$C_4$ alkyl; and
$R_3$ is hydrogen, alkyl, aromatic or $CF_3$,
and further in which any phenyl or fused benzo may optionally be substituted with hydrogen, halogen, CN, $NO_2$, $C_1$-$C_4$ alkyl, azido or $CF_3$.

4. The method of claim 3 in which each $R_1$ and $R_2$ is independently hydrogen, halogen, CN, $NO_2$, alkyl, phenyl, azido or $CF_3$.

5. The method of claim 3 in which at least one of $R_1$ and $R_2$ is other than hydrogen.

6. The method of claim 5 in which both of $R_1$ and $R_2$ are other than hydrogen.

7. The method of claim 6 in which both $R_1$ and $R_2$ are Cl.

8. The method of claim 3 in which the compound is a tetrazole compound.

9. The method of claim 8 in which at least one of $R_1$ and $R_2$ is other than hydrogen.

10. The method of claim 3 in which the compound is a triazole compound.

11. The method of claim 10 in which $A_1$ is C and both of $A_2$ and $A_3$ are N.

12. The method of claim 11 in which at least one of $R_1$ and $R_2$ is other than hydrogen.

13. A method for providing neuroprotection in a mammal requiring protection from increased excitatory amino acid neurotransmission which comprises administering to the mammal a neuroprotective amount of a compound having the general structure:

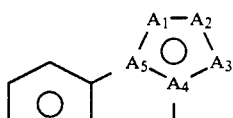
(I)

or

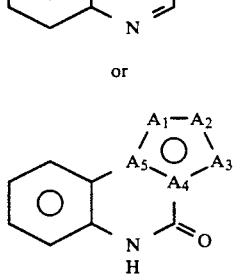
(II)

a tautomer thereof, or a pharmaceutically acceptable salt thereof, in which
each of $A_1$, $A_2$ and $A_3$ is independently either C or N except that at least one of $A_1$, $A_2$ and $A_3$ is N; and $A_4$ is C and $A_5$ is N.

14. The method of claim 13 and which comprises administering a compound selected from the group consisting of:

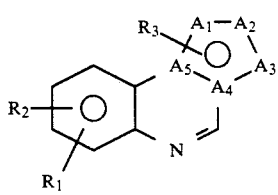
(III)

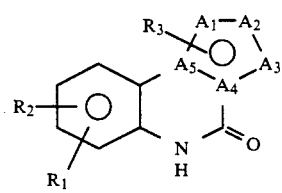
(IV)

a tautomer thereof, and a pharmaceutically acceptable salt thereof, in which:
$A_{1-5}$ are as previously defined;
each of $R_1$ and $R_2$ is independently hydrogen, halogen, CN, $NO_2$, $C_1-C_4$ alkyl, phenyl or fused benzo, azido, $CF_3$, $NHSO_2R'$ with $R'$ comprising $C_1-C_4$ alkyl or phenyl, or $SO_2NR''R'''$ with each of $R''$ and $R'''$ being either H or a $C_1-C_4$ alkyl; and
$R_3$ is hydrogen, alkyl, aromatic or $CF_3$,
and further in which any phenyl or fused benzo may optionally be substituted with hydrogen, halogen, CN, $NO_2$, $C_1-C_4$ alkyl, azido or $CF_3$.

15. The method of claim 14 in which each $R_1$ and $R_2$ is independently hydrogen, halogen, CN, $NO_2$, alkyl, phenyl, azido or $CF_3$.

16. A method for treating neurological disorders selected from the group consisting of epilepsy, stroke, brain and spinal cord trauma, cerebral ischaemia, muscular spasms, Huntingdon's chorea, dementia of the Alzheimer's type, Parkinson's disease, Amyotrophic lateral sclerosis, anxiety, urinary incontinence, analgesia, muscle spasms, opiate tolerance and withdrawal, and psychosis in a mammal in need of such treatment which comprises administering to the mammal a pharmaceutically effective amount of a compound having the general structure:

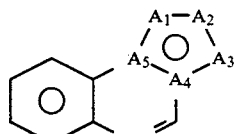
(I)

or

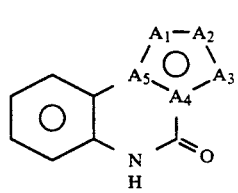
(II)

a tautomer thereof, or a pharmaceutically acceptable salt thereof, in which:
each of $A_1$, $A_2$ and $A_3$ is independently either C or N except that at least one of $A_1$, $A_2$ and $A_3$ is N; and $A_4$ is C and $A_5$ is N.

17. The method of claim 16 and which comprises administering a compound selected from the group consisting of:

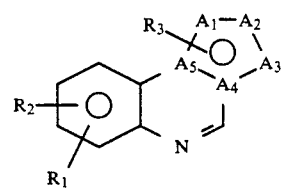
(III)

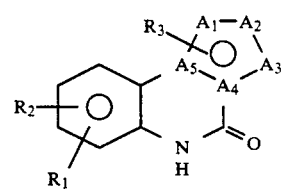
(IV)

a tautomer thereof, and a pharmaceutically acceptable salt thereof, in which:
$A_{1-5}$ are as previously defined;
each of $R_1$ and $R_2$ is independently hydrogen, halogen, CN, $NO_2$, $C_1-C_4$ alkyl, phenyl or fused benzo, azido, $CF_3$, $NHSO_2R'$ with $R'$ comprising $C_1-C_4$ alkyl or phenyl, or $SO_2NR''R'''$ with each of $R''$ and $R'''$ being either H or a $C_1-C_4$ alkyl; and
$R_3$ is hydrogen, alkyl, aromatic or $CF_3$,
and further in which any phenyl or fused benzo may optionally be substituted with hydrogen, halogen, CN, $NO_2$, $C_1-C_4$ alkyl, azido or $CF_3$.

18. The method of claim 17 in which each $R_1$ and $R_2$ is independently hydrogen, halogen, CN, $NO_2$, alkyl, phenyl, azido or $CF_3$.

* * * * *

UNITED STATES PATENT AND TRADEMARK OFFICE
CERTIFICATE OF CORRECTION

PATENT NO.    :    5,153,196

DATED         :    October 6, 1992

INVENTOR(S)   :    Loretta A. McQuaid; Charles H. Mitch;
                   Paul L. Ornstein; Darryle D. Schoepp;
                   Edward C. R. Smith It is certified that an error appears in the above-identified patent and that said Letters Patent is hereby corrected as shown below:

In the ABSTRACT, "or more EAA receptors, as neurological disorders" should read --or more EAA receptors, as neuroprotective agents, and in the treatment of various neurological disorders--.

Column 8, Structure (V)

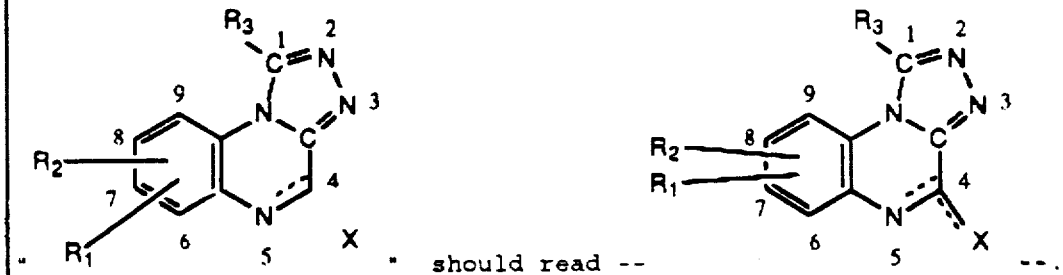

should read --

Colum 12, Structure (VI)

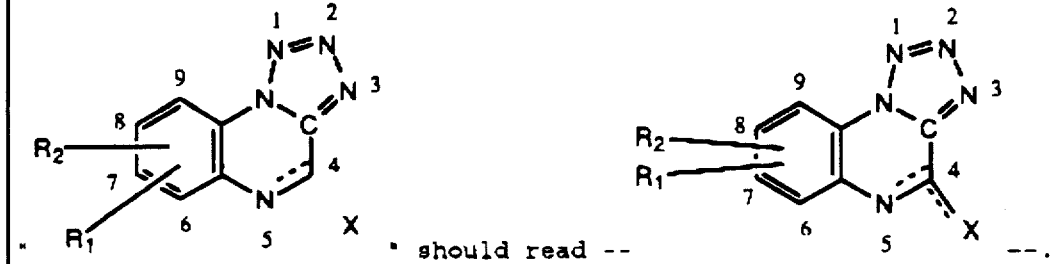

should read --

Column 20, line 15, "2. The method of claim 1 which the compound is a" should read --2. The method of claim 1 in which the compound is a--.

UNITED STATES PATENT AND TRADEMARK OFFICE
CERTIFICATE OF CORRECTION

PATENT NO. : 5,153,196

DATED : October 6, 1992

INVENTOR(S) : Lorretta A. McQuaid; Charles H. Mitch; Paul L. Ornstein; Darryle D. Schoepp, Edward C. R. Smith It is certified that error appears in the above-identified patent and that said Letters Patent is hereby corrected as shown below:

Column 21, line 67, "muscular spasms, Huntingdon's chorea, dementia of the" should read --muscular spasms, Huntington's chorea, dementia of the--.

Signed and Sealed this

Ninth Day of November, 1993

Attest:

BRUCE LEHMAN

Attesting Officer

Commissioner of Patents and Trademarks